United States Patent
Li et al.

(10) Patent No.: US 9,485,970 B2
(45) Date of Patent: Nov. 8, 2016

(54) **SELECTIVE BREEDING METHOD OF A NEW STRAIN OF *CRASSOSTREA GIGAS* WITH ORANGE LEFT AND RIGHT SHELLS**

(71) Applicant: OCEAN UNIVERSITY OF CHINA, Qingdao (CN)

(72) Inventors: Qi Li, Qingdao (CN); Rihao Cong, Qingdao (CN); Weijun Wang, Yantai (CN)

(73) Assignee: OCEAN UNIVERSITY OF CHINA, Qingdao (CN)

( * ) Notice: Subject to any disclaimer, the term of this patent is extended or adjusted under 35 U.S.C. 154(b) by 0 days.

(21) Appl. No.: 14/911,885

(22) PCT Filed: Apr. 16, 2014

(86) PCT No.: PCT/CN2014/075464
§ 371 (c)(1),
(2) Date: Apr. 11, 2016

(87) PCT Pub. No.: WO2015/021785
PCT Pub. Date: Feb. 19, 2015

(65) Prior Publication Data
US 2016/0242395 A1 Aug. 25, 2016

(30) Foreign Application Priority Data
Aug. 16, 2013 (CN) .......................... 2013 1 0355996

(51) Int. Cl.
*A01K 61/00* (2006.01)
*A01K 67/00* (2006.01)

(52) U.S. Cl.
CPC ............ *A01K 61/002* (2013.01); *A01K 61/001* (2013.01); *A01K 67/00* (2013.01)

(58) Field of Classification Search
None
See application file for complete search history.

(56) References Cited

U.S. PATENT DOCUMENTS

2010/0162964 A1   7/2010   Yan et al.

FOREIGN PATENT DOCUMENTS

| CN | 101292635 A | 10/2008 |
|----|-------------|---------|
| CN | 103416336 A | 12/2013 |
| JP | 2005333914 A | 12/2005 |

OTHER PUBLICATIONS

Brake, J. et al., "Evidence for genetic control of pigmentation of shell and mantle edge in selected families of Pacific oysters, *Crassostrea gigas*", 2004, Aquaculture, vol. 229: pp. 89-98.*
Evans, S. et al., "Heritability of shell pigmentation in the Pacific oyster, *Crassostrea gigas*", Aquaculture, 2009, vol. 286: pp. 211-216.*
International Search Report (PCT/ISA/210) issued on Jul. 22, 2014, by the State Intellectual Property Office of China as the International Searching Authority for International Application No. PCT/CN2014/075464.

* cited by examiner

*Primary Examiner* — Michael Burkhart
(74) *Attorney, Agent, or Firm* — Buchanan Ingersoll & Rooney PC

(57) ABSTRACT

A selective breeding method of a new strain of *Crassostrea gigas* with orange left and right shells includes: selecting individuals of *C. gigas* with purple left shell and black mantle as the male broodstocks and individuals of *C. gigas* with black left shell and black mantle as the female broodstocks from cultured populations to generate a F1 family by applying single-pair mating strategy; selecting individuals with black purple left and right shells and black mantle from the F1 family as broodstocks to generate F2 families through family selection; selecting individuals with black purple left and right shells and black mantle from the F2 families as broodstocks to generate F3 families through family selection; and selecting individuals with orange left and right shells from the F3 families as broodstocks to propagate to generate a new strain of *C. gigas* with the stably inherited trait of orange left and right shells.

4 Claims, No Drawings

SELECTIVE BREEDING METHOD OF A NEW STRAIN OF *CRASSOSTREA GIGAS* WITH ORANGE LEFT AND RIGHT SHELLS

FIELD OF THE INVENTION

The present invention relates to a family selective breeding technique of shellfish, and particularly, relates to a selective breeding method of a new strain of *Crassostrea gigas* with orange left and right shells.

BACKGROUND OF THE INVENTION

The Pacific oyster (*Crassostra gigas*) belonging to phylum Mollusca, class Bivalvia, order Ostreoida, family Ostreidae, genus *Crassostrea*, has advantages of strong adaptability to environment, rapid growth, good taste and high nutritive, and is ranked as the top cultured commercial shellfish with the largest production and the widest distribution in the world. As the most widely farmed shellfish in the world, its industry largely relies on hatchery-produced seed, and all of the broodstock used in hatcheries is sourced from wild populations which have never undergone genetic improvement.

As an economically important trait, the shell color of *C. gigas* has attracted the interest of geneticists and breeders due to its stable inheritance. In the wild populations of *C. gigas*, individuals with black, white or golden shell color are common, while no individuals with orange shell color have been found. So far, there is no report on the selective breeding methods of *C. gigas* with orange left and right shells.

SUMMARY OF THE INVENTION

The objective of the present invention is to provide a selective breeding method of a new strain of *C. gigas* with orange left and right shells. This new strain has an obvious phenotypic trait, namely the orange left and right shells. These oysters with orange shell color shells are more popular in market, and sold at higher price than others.

In order to fulfill the above-described objective, the selective breeding method of the new strain of *C. gigas* with orange left and right shells comprises the following steps:
(1) Selective breeding of the first generation (F1): selecting individuals of *C. gigas* with pure purple left shell and black mantle as the male broodstocks and individuals of *C. gigas* with pure black left shell and black mantle as the female broodstocks to generate a F1 family by applying single-pair mating strategy;
(2) Selective breeding of the second generation (F2): selecting individuals with black purple left and right shells and black mantle from the F1 family as broodstocks to generate F2 families through family selection;
(3) Selective breeding of the third generation (F3): selecting individuals with black purple left and right shells and black mantle from the F2 families as broodstocks to generate F3 families through family selection;
(4) Purification of the new strain: selecting individuals with orange left and right shells from the F3 families as broodstocks to propagate to generate a new strain of *C. gigas* with the stably inherited trait of orange left and right shells.
Particularly, the broodstocks described above are one to two years old *C. gigas* individuals with regular shell ranging from 10 to 12 cm in shell height.

Particularly, the strategy for generating the F1 family, the F2 families and the F3 families, and the purification of the new strain comprises the following steps:
A. Single-pair mating and hatching: identifying male and female broodstocks, and separating them into different groups; mating one female with one male to generate full-sib families; putting fertilized eggs obtained from each family separately into 100 L polyethylene plastic buckets filled with filtered seawater; marking on the polyethylene plastic buckets and aerating the seawater slightly; controlling the stocking density at 20-40 eggs/mL and the seawater temperature at 20-24° C. After 18-20 h incubation, the fertilized eggs develop into D-shaped larvae.
B. Larvae culture: selecting the D-shaped larvae with 300 mesh sieve by siphonage and cultivating them in 100 L polyethylene plastic buckets separately. Stocking density is decreased with larval growth. To be specific, the density is initially set to 10-15 larvae/mL at early stage when the shell height of the larvae is less than 120 µm, controlled at 5-10 larvae/mL when the shell height increases from 120 to 150 µm, maintained at less than 5 larvae/mL when the shell height ranges from 150 to 200 µm, and reduced to 2 larvae/mL when the shell height increases to 250 to 300 µm.
C. Spats nursery: to avoid the contamination of wild *C. gigas* larvae in natural sea areas, cultivating all the families in outdoor nursery tank after all eyed larvae metamorphose to spats.
D. Offshore grow-out: transferring the spats of the families to the same sea area for cultivation after wild *C. gigas* larvae have finished attaching stage.

Furthermore, the water temperature in the step B is controlled from 20 to 24° C., and the salinity is maintained from 28 to 30 psu. Early larvae with shell height less than 120 µm are fed with *Isochrysis galbana* as initial feeds, and the larvae at later stages are fed with one or combinations of *Isochrysis galbana*, *Platymonas helgolandica* and *Chaetoceros calcitrans*. Meanwhile, mutual contamination among different families is strictly avoided.

Compared with the traditional practice, transgenic techniques and chemical treatment are not used in the selective breeding method. The new strain of *C. gigas* with orange left and right shells is obtained by artificial directional selection, and therefore not only enriches shell color characteristics of *C. gigas*, but also satisfies the demands of different groups of customers. The new color trait of *C. gigas* improves the additional value of oyster products, and the market price and the income of enterprises and farmers are raised correspondingly. It has been proven that there is a promising market for this new strain of *C. gigas*.

DETAILED EMBODIMENTS (1) Selective breeding of the first generation (F1):
1. Single-pair mating and hatching: selecting individuals of *C. gigas* with pure purple left shell and black mantle as the male broodstocks and individuals of *C. gigas* with pure black left shell and black mantle as the female broodstocks from cultured populations in 2009, and distinguishing male and female broodstocks into different groups; mating one female with one male to generate full-sib families; putting fertilized eggs obtained from each family separately into 100 L polyethylene plastic buckets filled with filtered seawater; marking on the polyethylene plastic buckets and aerating the seawater slightly; controlling the stocking density at 20-40 eggs/mL and the seawater temperature at 20-24° C. After 18-20 h incubation, the fertilized eggs develop into D-shaped larvae.

2. Larvae culture: selecting the D-shaped larvae with 300 mesh sieve by siphonage and cultivating them in 100 L polyethylene plastic buckets separately. Stocking density is decreased with larval growth. To be specific, at early stage when the shell height of the larvae is less than 120 μm, the density is set to 10-15 larvae/mL and the larvae are fed with *Isochrysis galbana* as initial feeds. The density is controlled at 5-10 larvae/mL when the shell height increases from 120 to 150 μm, maintained at less than 5 larvae/mL when the shell height ranges from 150 to 200 μm, and reduced to 2 larvae/mL when the shell height increases to 250 to 300 μm.

3. Spats nursery: to avoid the contamination of wild *C. gigas* larvae in natural sea areas, cultivating all the families in outdoor nursery tank after all eyed larvae metamorphose to spats.

4. Offshore grow-out: transferring the spats of the families to the same sea area for grow-out after wild *C. gigas* larvae have finished attaching stage.

(2) Selective breeding of the second generation (F2): selecting individuals with black purple left and right shells and black mantle from the F1 family as broodstocks in 2010, and other procedures are referred to those used in the selection of the first generation.

(3) Selective breeding of the third generation (F3): selecting individuals with black purple left and right shells and black mantle from the F2 families as broodstocks in 2011, and other procedures are referred to those used in the selection of the first generation.

(4) Purification and propagation of the new strain of *C. gigas* with orange left and right shells: selecting individuals with orange left and right shells from the F3 families as broodstocks in 2012 to propagate to generate a new strain of *C. gigas* with the stably inherited trait of orange left and right shells.

In this embodiment, the broodstocks selected are all one-year-old individuals with regular shell ranging from 10 to 12 cm in shell height. In the process of larval culture, the larvae are fed with *Isochrysis galbana* and *Platymonas helgolandica*, and cultivated at the temperature of 20-24° C. and salinity of 28-30 psu. Meanwhile, mutual contamination among different families is strictly avoided.

The present invention comprises the procedures including elaborate broodstock selection, family selection, larvae culture, spats nursery, offshore grow-out, trait purification and seed propagation, and finally generated a new strain of *C. gigas* with orange left and right shells through four generations' directional selection. One advantage of the present invention is to create a new commercial strain of *C. gigas* from the perspective of shell color—a rare type of *C. gigas* with orange shell through consecutive four generations of directional family selection rather than using transgenetic techniques and chemical treatment. Moreover, this new color trait improves the additional value of oyster products, and the market price and the income of enterprises and farmers are raised correspondingly. It has been proven that there is a promising market for this new strain of *C. gigas*.

One skilled in the art will understand that the embodiment of the present invention as described above is exemplary only and not intended to be limiting. It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

We claim:

1. A selective breeding method of a new strain of *Crassostrea gigas* with orange left and right shells, comprising the following steps:
   (1) selective breeding of a first generation (F1): selecting individuals of *C. gigas* with pure purple left shell and black mantle as male broodstocks and individuals of *C. gigas* with pure black left shell and black mantle as female broodstocks from cultured populations to generate a F1 family by applying single-pair mating strategy;
   (2) selective breeding of a second generation (F2): selecting individuals with black purple left and right shells and black mantle from the F1 family as broodstocks to generate F2 families through family selection;
   (3) selective breeding of a third generation (F3): selecting individuals with black purple left and right shells and black mantle from the F2 families as broodstocks to generate F3 families through family selection; and
   (4) purification of the new strain: selecting individuals with orange left and right shells from the F3 families as broodstocks to propagate to generate a new strain of *C. gigas* with stably inherited trait of orange left and right shells.

2. The selective breeding method according to the claim 1, wherein the broodstocks used are one to two years old *C. gigas* individuals with regular shell ranging from 10 to 12 cm in shell height.

3. The selective breeding method according to the claim 1, wherein generating the F1 family, the F2 family, the F3 family and the purification of the new strain comprises the following steps:
   A. single-pair mating and hatching: identifying male and female broodstocks, and separating them into different groups; mating one female with one male to generate full-sib families; putting fertilized eggs obtained from each family separately into 100 L polyethylene plastic buckets filled with filtered seawater; marking on the polyethylene plastic buckets and aerating the seawater slightly; controlling a stocking density at 20-40 eggs/mL and a seawater temperature at 20-24° C., the fertilized eggs developing into D-shaped larvae after 18-20 h incubation,
   B. larvae culture: selecting the D-shaped larvae with 300 mesh sieve by siphonage and cultivating them in 100 L polyethylene plastic buckets separately,
   C. spats nursery: cultivating all the families in an outdoor nursery tank after all eyed larvae metamorphose to spats, and
   D. offshore grow-out: transferring the spats of the families to the same sea area for cultivation after wild *C. gigas* larvae have finished attaching stage,
   wherein in the step B, a stocking density is decreased with larval growth, a density being initially set to 10-15 larvae/mL at a stage when a shell height of the larvae is less than 120 μm, controlled at 5-10 larvae/mL when a shell height increases from 120 to 150 μm, maintained at less than 5 larvae/mL when a shell height ranges from 150 to 200 μm, and reduced to 2 larvae/mL when a shell height increases to 250 to 300 μm.

4. The selective breeding method according to the claim 3,
   wherein in the step B, a water temperature is controlled from 20 to 24° C., and a salinity is maintained from 28 to 30 psu, wherein in the step B, early larvae with a shell height less than 120 μm are fed with *Isochrysis galbana* as initial feeds, and larvae at later stages are fed with at least one of *Isochrysis galbana, Platymonas helgolandica* and *Chaetoceros calcitrans*, and wherein the step B is free of mutual contamination among different families.

\* \* \* \* \*